United States Patent [19]

Steiner

[11] Patent Number: 4,945,085

[45] Date of Patent: Jul. 31, 1990

[54] USE OF SUCRALFATE FOR CONTROLLING EMESIS AND/OR DIARRHEA

[75] Inventor: Kurt Steiner, Grafing, Fed. Rep. of Germany

[73] Assignee: Merck Patent Gesellschaft Mit Beschränkter Haftung, Darmstadt, Fed. Rep. of Germany

[21] Appl. No.: 622,510

[22] Filed: Jun. 20, 1984

[30] Foreign Application Priority Data

Jun. 20, 1983 [DE] Fed. Rep. of Germany ....... 3322078

[51] Int. Cl.$^5$ ............................................. A61K 31/70
[52] U.S. Cl. ........................................ 514/53; 514/23
[58] Field of Search ...................... 424/180; 514/53, 23

[56] References Cited

U.S. PATENT DOCUMENTS 3,432,489  3/1969  Nitta et al.
4,378,353  3/1983  Goegelman et al. ................ 536/7.1

OTHER PUBLICATIONS

Taber's Cyclopedic Medical Dictionary, pp. 465–466, and 1065.
Maas et al, Southern Medical Journal, vol. 76, No. 1, p. 98, 1983.
"Ulcerlmin", Chemical Abstracts, Matsuo, Hiroshi, vol. 90, p. 3, No. 15891y.
Chemical Abstracts, Tenth Collective Index, vols. 86–95, 1977–1981, American Counsel Soc., p. 1897CS.
"Sucralfate: New Aspects in Therapy of Ulcers and Lesions . . . ", Chemical Abstracts, vol. 99, p. 100, No. 187725z.
Physician's Desk Reference, 38th Edition, 1984, p. (2), 1164–1165.

Primary Examiner—John W. Rollins
Assistant Examiner—Elli Peselev
Attorney, Agent, or Firm—Millen, White & Zelano

[57] ABSTRACT

Sucralfate can be used to control and treat emesis and/or diarrhea in veterinary medicine.

12 Claims, No Drawings

USE OF SUCRALFATE FOR CONTROLLING EMESIS AND/OR DIARRHEA

BACKGROUND OF THE INVENTION

This invention relates to the control of emesis and/or diarrhea in veterinary medicine.

There is a high incidence of emesis and diarrhea in veterinary medicine, including, and in particular, in practices specializing in small animals. However, there is a lack of suitable agents which are easy to use for these indications.

Sucralfate (CARAFATE® (tablets-USA) or ULCOGANT® (granules-FRG) β-D-Fructo furanosyl-γ-D-glucopyranoside octakis (hydrogen sulfate), aluminum complex is a basic aluminum sucrose sulfate. It is disclosed in German Offenlegungsschrift No. 1,568,346 whose disclosure is incorporated by reference herein and is used in human medicine to speed up the healing of ulcers and to alleviate the symptoms of peptic ulcers. An effect of sucralfate on emesis and/or diarrhea has not hitherto been disclosed. For current usage of sucralfate, see, e.g., Physicians' Desk Reference, 38th Ed. (1984) 1164–1165, whose disclosure is incorporated by reference herein.

SUMMARY OF THE INVENTION

It is an object of this invention to provide new ways of controlling emesis and/or diarrhea in veterinary medicine, and of making available suitable agents which are easy to use for these purposes.

Upon further study of the specification and appended claims, further objects and advantages of this invention will become apparent to those skilled in the art.

These objects have been achieved by the present invention based on the finding that sucralfate, which is well tolerated, is outstandingly suitable for the purposes indicated. Accordingly, this invention relates to the use of sucralfate for controlling emesis and/or diarrhea in veterinary medicine, i.e., to a method for treating emesis in a veterinary patient in need of such treatment comprising administering an effective amount of sucralfate to the patient, and to a method of treating diarrhea in a veterinary patient in need of such treatment comprising administering an effective amount of sucralfate to the patient. Both indications can also be treated at the same time.

DETAILED DISCUSSION

This invention is primarily applicable to treat small animals, preferably dogs and cats, but also, for example, calves, pigs (piglets) and animals in zoos. Sucralfate is preferably administered in single doses between 0.5 and 5, particularly preferably between 1 and 2, grams. This corresponds to about 25 to 250 mg/kg per dose. Cats and small dogs preferably each receive about 1 g, while larger dogs each receive about 2 g as a single dose. These single doses are particularly preferably administered once to thrice daily, in particular twice daily, in the morning and evening, for a period of 1 to 3 days, and longer if necessary until the symptoms disappear, preferably in the form of an aqueous suspension of sucralfate granules, which is administered buccally, retrolabially, using a syringe.

It is possible to employ the commercial forms of sucralfate for this mode of use. However, all the other customary forms for use in veterinary medicine are likewise suitable, for example, powders, capsules, tablets, coated tablets, syrups, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A poodle had suffered for nine days from vomiting, which was sometimes very violent, together with diarrhea. 1 g. of ULCOGANT® granules in the form of an aqueous suspension was administered retrolabially twice at an interval of 8 hours. The symptoms had disappeared within 24 hours.

EXAMPLE 2

A dog which had developed gastroenteritis induced by eating snow received oral administration of 2 grams of ULCOGANT® granules as an aqueous suspension for three days, in the morning and evening each day. It was subsequently free of symptoms.

EXAMPLE 3

A cat suffering from diarrhea was treated orally with 0.5 g. of ULCOGANT® in the form of an aqueous suspension thrice daily for two days. After this, the gastrointestinal disturbance had been eliminated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of treating emesis in an animal in need of such treatment comprising administering to the animal an effective amount of sucralfate.

2. A method of claim 1 wherein the animal is a dog or cat.

3. A method of claim 1 wherein the unit dosage administered is 1–2 g.

4. A method of claim 3 wherein the unit dose is administered 1–3 times daily.

5. A method of treating diarrhea in a veterinary animal in need of such treatment comprising administering to the animal an effective amount of sucralfate.

6. A method of claim 5 wherein the animal is a dog or cat.

7. A method of claim 5 wherein the unit dosage administered is 1–2 g.

8. A method of claim 7 wherein the unit dose is administered 1–3 times daily.

9. A method of simultaneously treating emesis and diarrhea in an animal in need of such treatment comprising administering to the animal an effective amount of sucralfate.

10. A method of claim 9 wherein the animal is a dog or cat.

11. A method of claim 9 wherein the unit dosage administered is 1–2 g.

12. A method of claim 11 wherein the unit dose is administered 1–3 times daily.

* * * * *